(12) United States Patent
Bushman et al.

(10) Patent No.: US 8,385,730 B2
(45) Date of Patent: Feb. 26, 2013

(54) AIR CARE UNIT ALLOWING FOR CUSTOMIZATION OF FRAGRANCE STRENGTH AND CHARACTER

(75) Inventors: Donald W. Bushman, Caledonia, MI (US); Kalliopi S. Haley, Byron Center, MI (US); Robert D. Faber, Grand Rapids, MI (US); David M. Flower, Caledonia, MI (US); Douglas K. Feenstra, Wyoming, MI (US)

(73) Assignee: Access Business Group International LLC, Ada, MI (US)

( * ) Notice: Subject to any disclaimer, the term of this patent is extended or adjusted under 35 U.S.C. 154(b) by 765 days.

(21) Appl. No.: 12/512,088

(22) Filed: Jul. 30, 2009

(65) Prior Publication Data

US 2010/0025490 A1 Feb. 4, 2010

Related U.S. Application Data

(60) Provisional application No. 61/137,496, filed on Jul. 30, 2008.

(51) Int. Cl.
*A01G 13/06* (2006.01)
(52) U.S. Cl. .................. 392/386; 392/390; 392/394
(58) Field of Classification Search .................. None
See application file for complete search history.

(56) References Cited

U.S. PATENT DOCUMENTS

| | | | |
|---|---|---|---|
| 4,006,841 A | 2/1977 | Alticosalian | |
| 4,035,451 A * | 7/1977 | Tringali | 261/101 |
| 4,549,674 A | 10/1985 | Alticosalian | |
| 4,691,850 A | 9/1987 | Kirschmann | |
| 5,133,042 A * | 7/1992 | Pelonis | 392/365 |
| 5,259,062 A * | 11/1993 | Pelonis | 392/365 |
| 5,565,148 A | 10/1996 | Pendergrass | |
| 5,805,768 A * | 9/1998 | Schwartz et al. | 392/390 |
| 5,898,475 A | 4/1999 | Martin | |
| 6,554,203 B2 | 4/2003 | Hess | |
| 6,619,559 B2 * | 9/2003 | Wohrle | 239/34 |
| 6,783,117 B2 * | 8/2004 | Wohrle | 261/26 |
| 6,925,252 B2 * | 8/2005 | Zhang et al. | 392/403 |
| 6,950,607 B2 * | 9/2005 | Yip et al. | 392/395 |
| 7,100,841 B2 | 9/2006 | Ivey | |
| 7,132,084 B1 * | 11/2006 | Roumpos | 422/125 |
| 7,152,809 B2 * | 12/2006 | Ketcha et al. | 239/13 |
| 7,223,166 B1 * | 5/2007 | Wiseman et al. | 454/337 |
| 7,389,943 B2 * | 6/2008 | Jaworski | 239/102.2 |
| 7,410,269 B2 | 8/2008 | Harrity | |
| 7,469,844 B2 * | 12/2008 | Conway et al. | 239/102.2 |
| 7,499,632 B2 * | 3/2009 | Granger et al. | 392/386 |
| 7,537,647 B2 * | 5/2009 | Adair et al. | 96/62 |
| 7,734,159 B2 * | 6/2010 | Beland et al. | 392/390 |
| 7,962,017 B2 * | 6/2011 | Viera | 392/392 |
| 8,137,629 B2 * | 3/2012 | Faber et al. | 422/120 |
| 8,170,405 B2 * | 5/2012 | Harris | 392/392 |
| 2002/0066798 A1 * | 6/2002 | Laudamiel-Pellet et al. | 239/34 |
| 2006/0081721 A1 | 4/2006 | Caserta | |

\* cited by examiner

*Primary Examiner* — Thor Campbell
(74) *Attorney, Agent, or Firm* — Alticor Inc.

(57) ABSTRACT

An air freshener with customizable fragrances is disclosed. The air freshener accepts a plurality of fragrance modules, which allow a user to create customized fragrant environments. A fan and/or heating element are included to increase fragrance dispersal. Additional components may be included into the air freshener to provide enhancements to the user experience, including but not limited to a clock, timer, or a music player. The air freshener obtains power from a number of sources, such as AC mains or DC batteries. Energy storage devices located on board the air freshener may be charged by inductive or solar power. The air freshener may also include lighting elements and styling cues to integrate into the local environment.

20 Claims, 14 Drawing Sheets

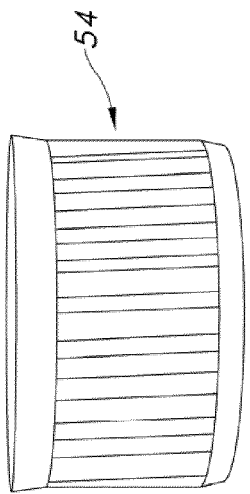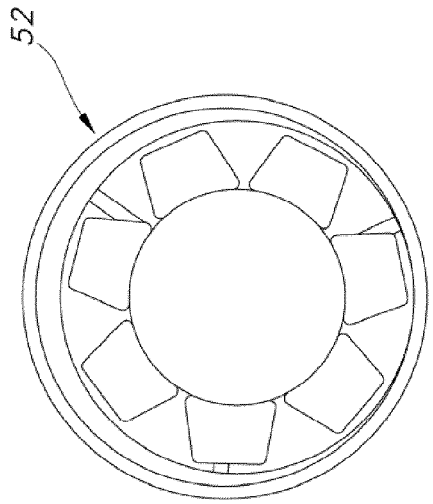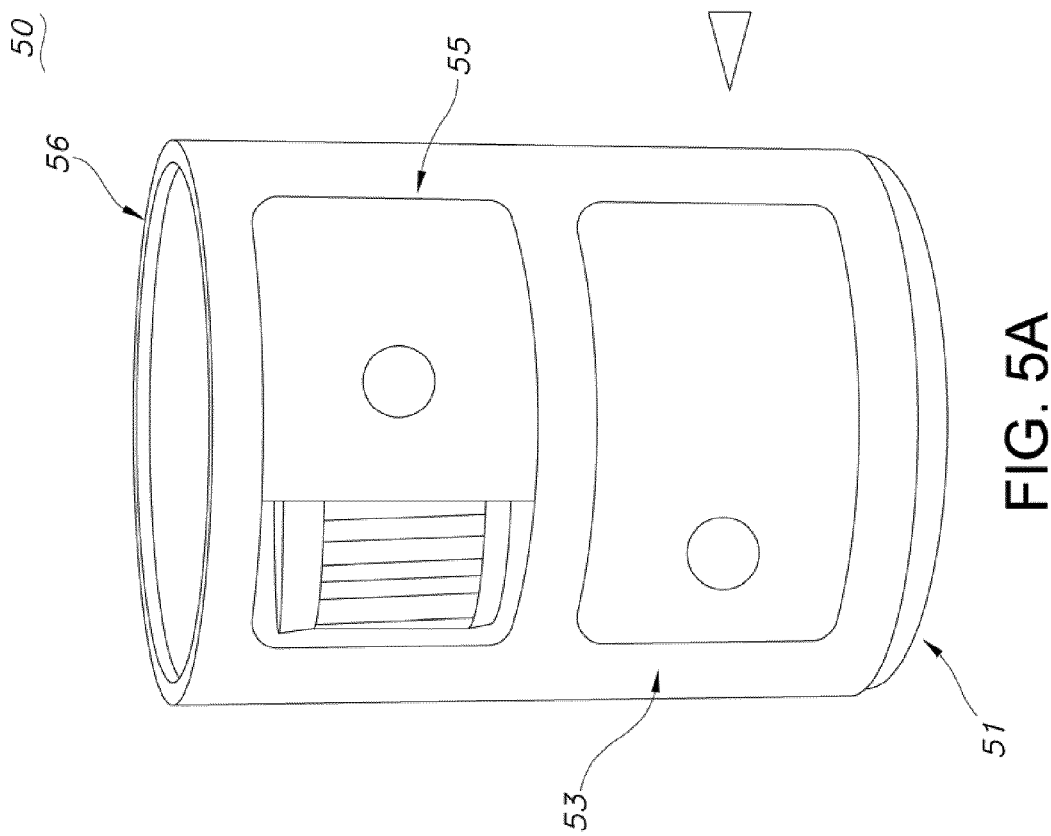

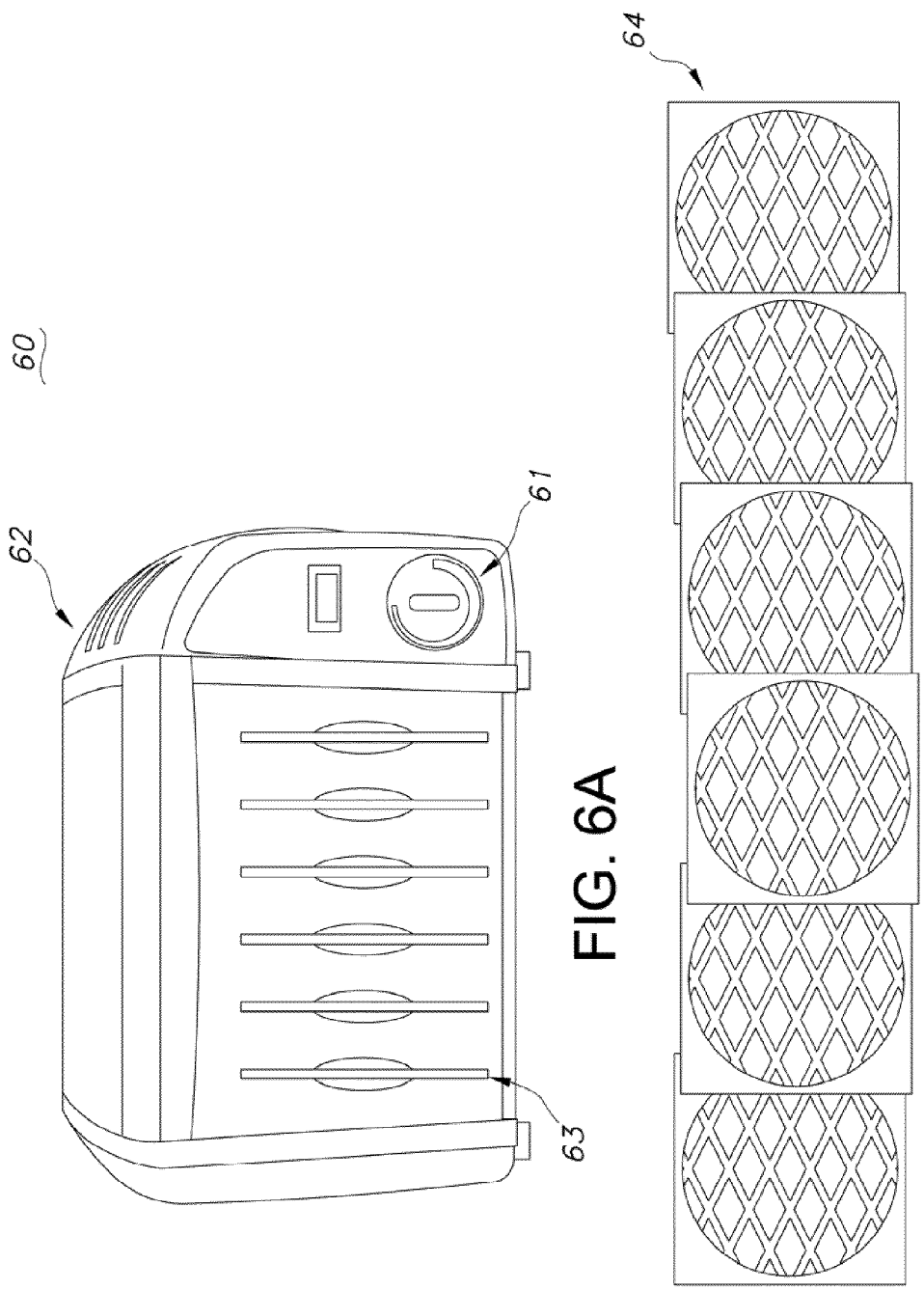

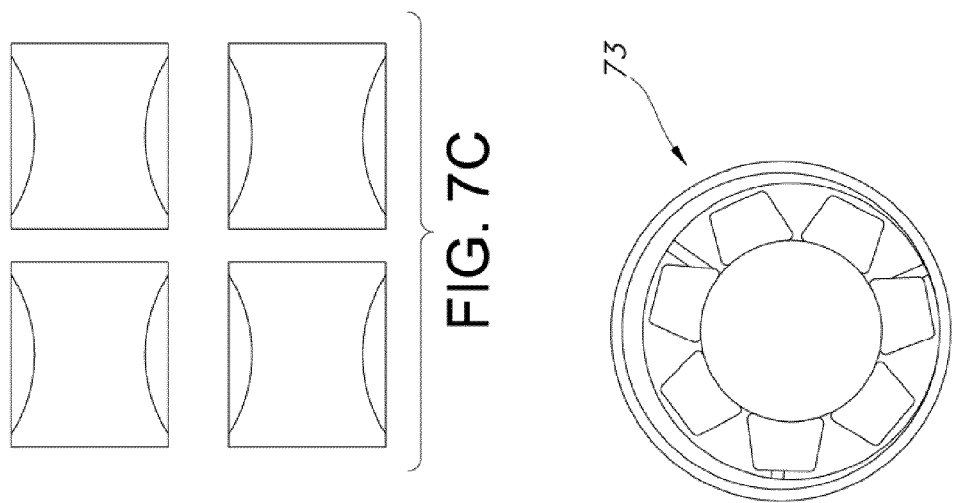
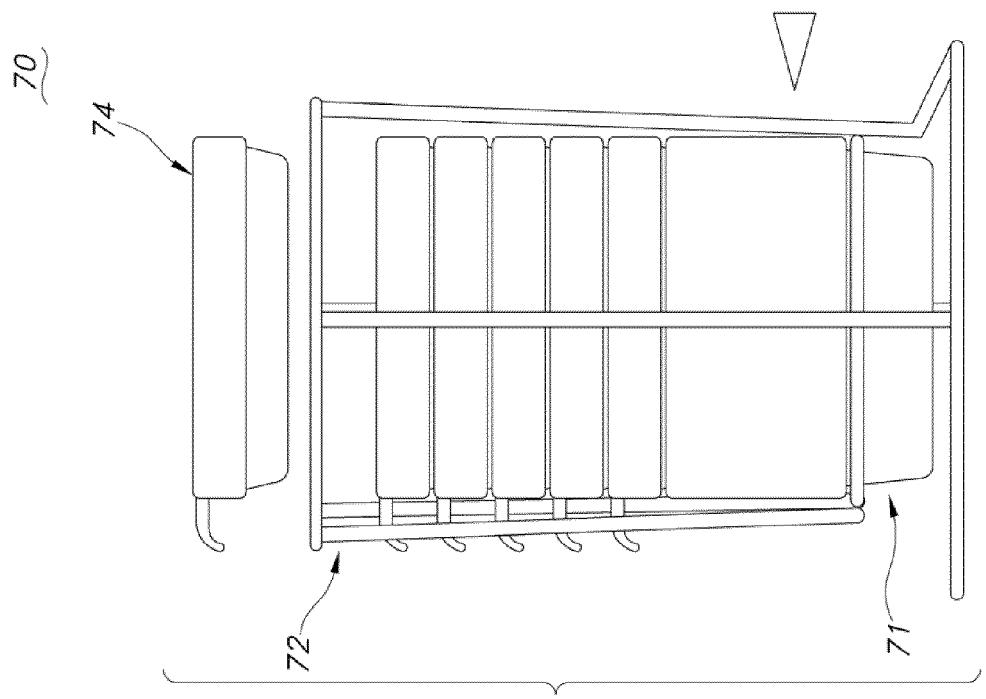

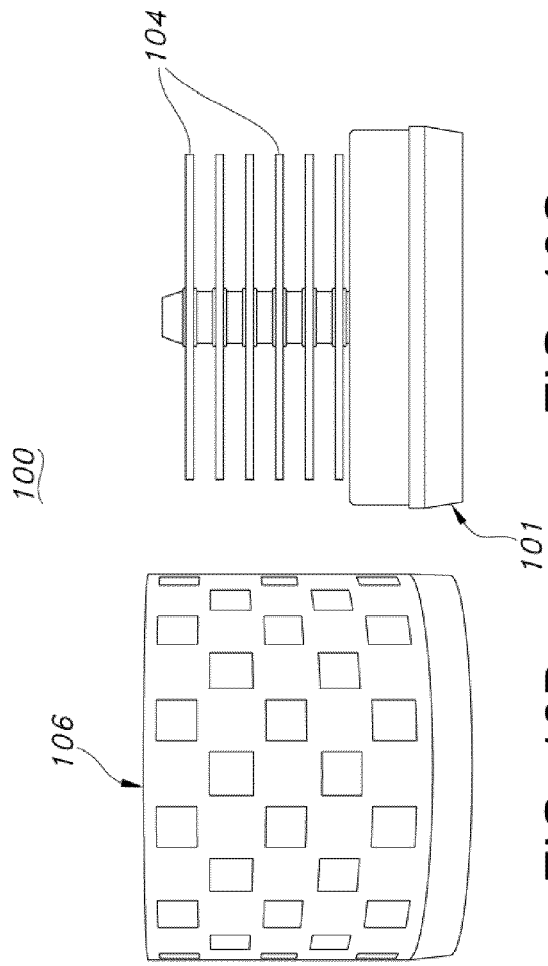
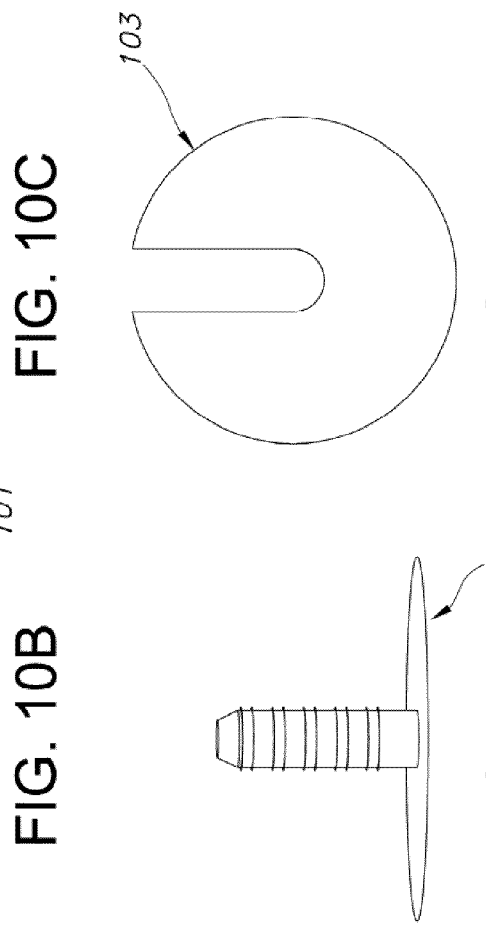
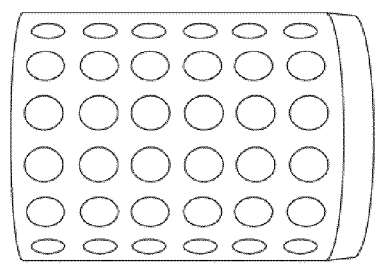
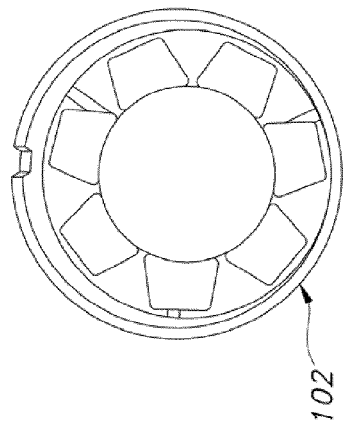
FIG. 10A  FIG. 10B  FIG. 10C  FIG. 10D  FIG. 10E  FIG. 10F

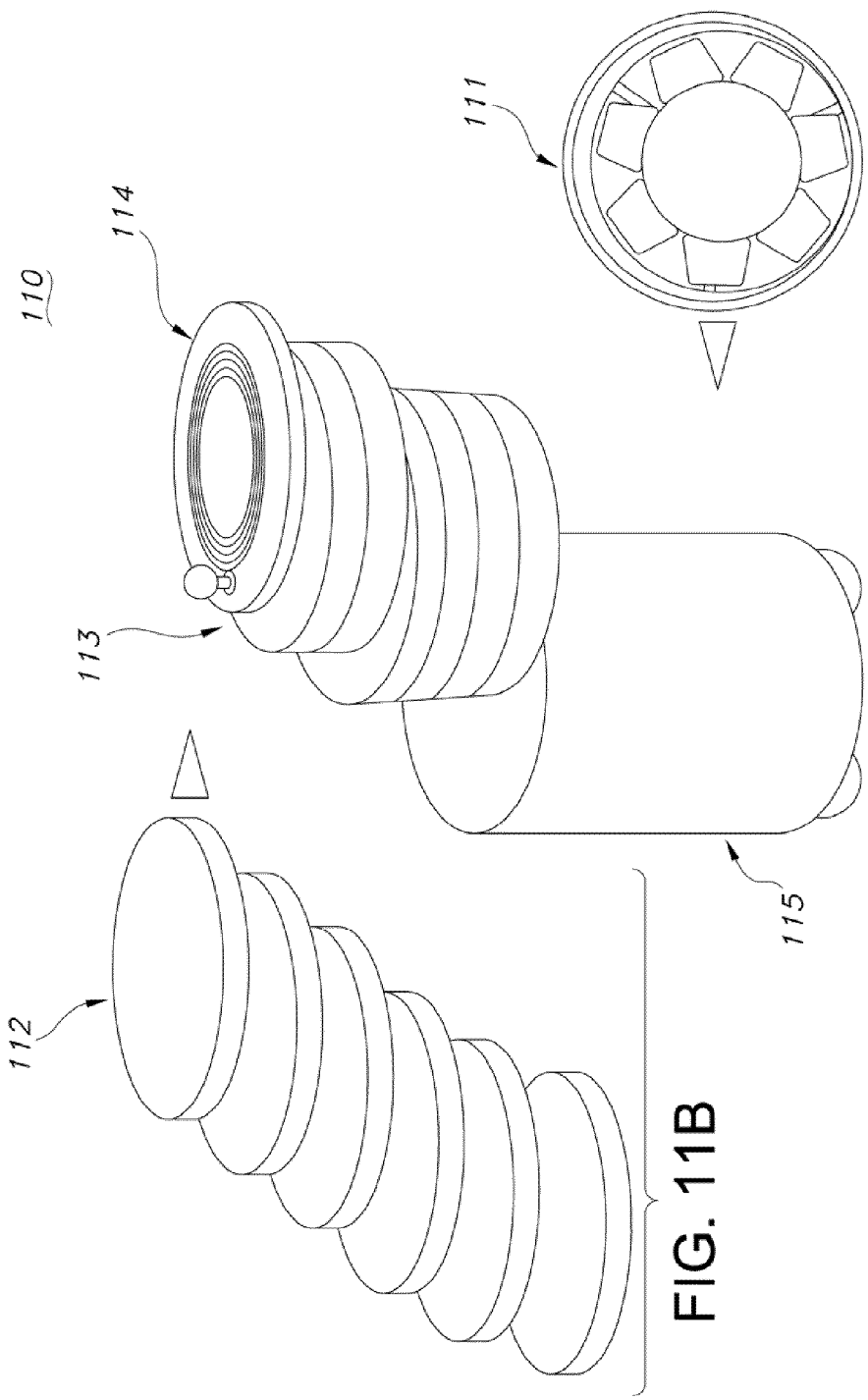

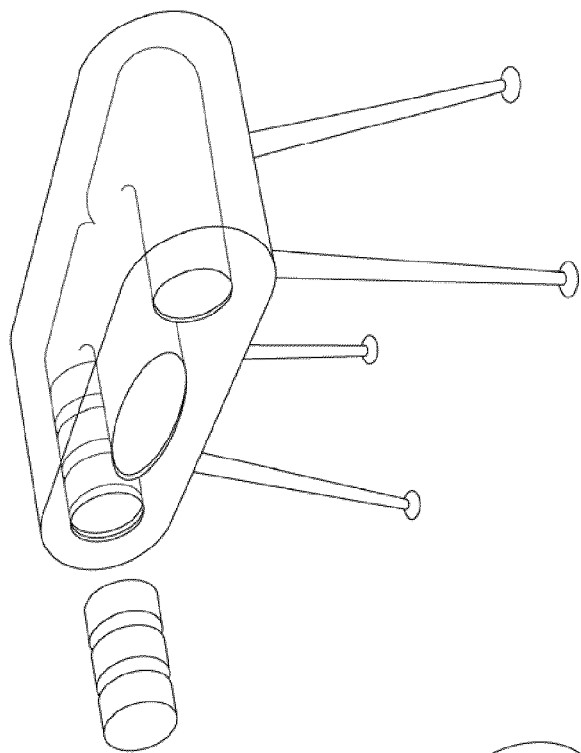
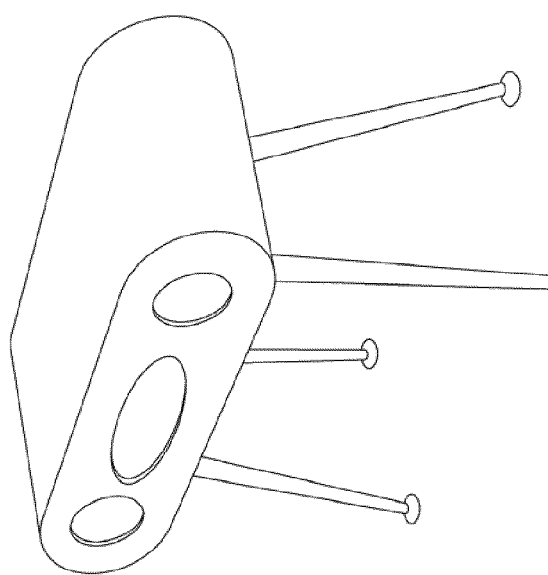
FIG. 14B
FIG. 14A

AIR CARE UNIT ALLOWING FOR CUSTOMIZATION OF FRAGRANCE STRENGTH AND CHARACTER

This application claims the benefit of U.S. Provisional Patent Application 61/137,496 which was filed on Jul. 30, 2008, which is herein incorporated by reference in its entirety.

BACKGROUND OF THE DISCLOSURE

This disclosure relates to air fresheners and devices which broadcast or disperse a scent or fragrance into an environment. More particularly, this disclosure relates to an air freshener unit which allows a user to adjust fragrance strength or intensity and also to customize the fragrance by mixing a variety of unique fragrances to the user's taste.

Air fresheners come in a variety of shapes and sizes. Some are un-powered, relying chiefly on evaporation to dispense fragrance, or scent, in an environment. Others use electrical power to heat the fragrance delivery means, which may be called a module, containing a volatile or vaporizable substance, in solid, semi-solid (gel), or liquid form. Still other air fresheners use forced air, by way of a fan or other means to increase airflow velocity in the presence of a scent module to enhance the fragrance delivery to the environment.

Many air fresheners are single-fragrance type, due to their design, whereby a module is inserted into a single repository, usually after some initial setup is done by the user, such as removing a packaging seal. There is no provision for additional modules in these devices, whether they are of the same fragrance or a contrasting or complimentary fragrance. Therefore, if a user desires to add more than one fragrance to the environment, a second, third, or even more air fresheners must be added, which is costly, and in the case of power outlet-based air fresheners, may occupy additional electrical outlets and also consumes more electricity.

What is needed then, is an air freshener that allows a user to customize the intensity and types of fragrances to be released into the environment. By adding or subtracting fragrance modules, the user is easily able to create customized fragrances to meet their expectations. For example, a user may wish to have a very intense fragrance released into the environment, such as apple blossom, which is not achievable using only one fragrance module. In another example, a user may wish to create a more complex fragrance environment by using at least one apple blossom module, at least one jasmine module, and even more additional modules to create a "garden" fragrant environment of contrasting or complimentary fragrances.

The air freshener of the present disclosure includes multiple fragrance modules and module locations, which are conveniently located close to a fan and/or heating element, for assisting the vaporization of the volatile components of the fragrances. The module locations, or receptacles, allow a user to easily install or replace fragrance modules while still locating the modules in alignment with air flow from the fan or heat from the heating element. The fan and/or heating element accelerates the dispersal of the fragrances contained with the fragrance modules so that the user can quickly achieve the desired fragrant environment.

The air freshener may be powered by electricity, including inductive power, disposable or rechargeable battery, or solar cell array. Power will be provided to at least a fan or heating element, as well as optional devices such as a light source, clock/alarm, or audio device, such as a radio or MP3 player. A combination of a fan and a heating element may be used to provide accelerated fragrance dispersal. In one embodiment, the air freshener will include audio components for music, including an AM/FM tuner (or other band receiver) or an MP3 or other audio input connection. Inductive power may be used to transfer power from an air freshener base portion to an operating portion, containing the fan and/or heating element, fragrance modules, and other controls and features, including an energy storage device. Additionally, the air freshener may obtain power inductively from a separate and unique inductive power location, such as a universal charging pad. A solar array may also be used to charge the air freshener's onboard energy storage devices. The array may be located in an advantageous location on the air freshener to receive solar energy, such as the top vertical surface.

The air freshener may also allow for programmable features, such as time delay, day/night activity, scent conservation by detecting motion or heat of users in the vicinity, among other features. In one embodiment, the air freshener uses an integral light source to compliment the dispersal of fragrances. For example, an array of light emitting diodes (LEDs) contained within the air freshener are activated by the device's control unit in response to fragrance dispersal or separately as artful display of color. In another embodiment, a clock/alarm is used to display time for the user's convenience, but also may be used to program the operation of the air freshener. For example, the air freshener may be programmed to provide fragrance for the user waking in the morning or when the user is schedule to arrive from work. In another embodiment, the air freshener utilizes sensors to determine if users are in the vicinity. If so, the freshener operates normally. If not, the freshener switches to an energy-conserving mode which also conserves the fragrance modules.

For a better understanding of the present invention, together with other and further features and advantages thereof, reference is made to the following description, taken in conjunction with the accompanying drawings, and the scope of the disclosure will be laid out in the claims.

It will be readily understood that the components of the present disclosure, as generally described and illustrated in the figures herein, may be arranged and designed in a wide variety of different configurations. Thus, the following more detailed description of the embodiments of the apparatus, system, and method of the present disclosure, as represented in accompanying figures, is not intended to limit the scope of the disclosure, as claimed, but is merely representative of selected embodiments of the disclosure.

Reference throughout this specification to "one embodiment" or "an embodiment" (or similar) means that a particular feature, structure, or characteristic described in connection with the embodiment is included in at least one embodiment of the present disclosure. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. In the following description, numerous specific details are provided, such as examples, to provide a thorough understanding of embodiments of the present disclosure. One skilled in the art will recognize, however, that the disclosure can be practiced without one or more of the specific details, or with other methods, components, materials, etc. In other instances, well-known structures, materials, or operations are not shown or described in detail to avoid obscuring aspects of the disclosure.

The illustrated embodiments of the disclosure will be best understood by reference to the drawings, wherein like parts are designated by like numerals or other labels throughout. The following description is intended only by way of example, and simply illustrates certain selected embodiments of devices, systems, and processes that are consistent with the disclosure as claimed herein.

BRIEF DESCRIPTION OF THE DRAWINGS

FIG. 5a is an illustrative view of one embodiment of the air freshener of the present disclosure.

FIG. 5b is a top illustrative view of a fan module for use in at least one embodiment of the present disclosure.

FIG. 5c is a side illustrative view of a fragrance module for use in at least one embodiment of the present disclosure.

FIG. 6a is an illustrative view of one embodiment of the air freshener of the present disclosure.

FIG. 6b is an illustrative view of a number of fragrance modules for use in at least one embodiment of the present disclosure.

FIG. 7a is an illustrative view of one embodiment of the air freshener of the present disclosure.

FIG. 7b is an illustrative view of a fan module for use with at least one embodiment of the air freshener of the present disclosure.

FIG. 7c is an illustrative view of a number of fragrance modules of at least one embodiment of the present disclosure.

FIG. 10a is a side view of one embodiment of the air freshener of the present disclosure.

FIG. 10b is an alternative side view of one embodiment of the air freshener of the present disclosure.

FIG. 10c is a side view of the base portion of the embodiment showing a number of fragrance disk modules supported by a center portion.

FIG. 10d is a top view of the fan module of at least one embodiment of the present disclosure.

FIG. 10e is a side view of the fragrance module holder of the embodiment showing a number of engagement locations for fragrance module disks.

FIG. 10f is a top view of a fragrance module according to at least one embodiment of the disclosure, including a channel contained within the disk for engaging the module holder.

FIG. 11a is an illustrative view of one embodiment of the air freshener of the present disclosure.

FIG. 11b is an illustrative view of a number of fragrance modules according to one embodiment of the air freshener of the present disclosure.

FIG. 11c is a top view of the fan module of at least one embodiment of the present disclosure.

FIG. 14a is an illustrative view of one embodiment of the air freshener of the present disclosure.

FIG. 14b is a cutaway view of the embodiment showing a fragrance module positioned to be installed into the air freshener.

DETAILED DESCRIPTION OF THE DISCLOSURE

Figure 1A:
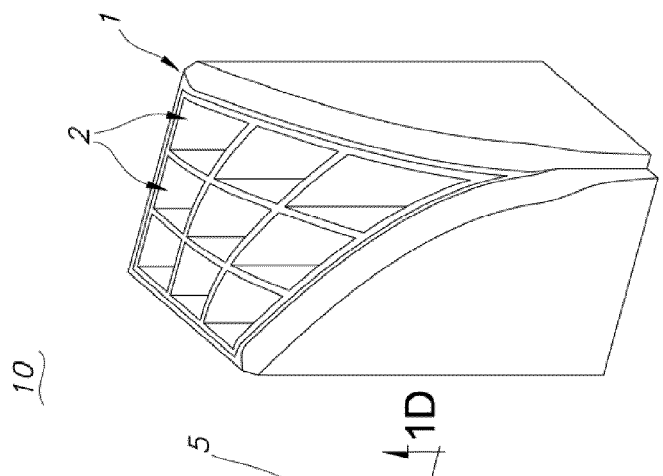
FIG. 1a is an illustrative view of one embodiment of the air freshener of the present disclosure showing fragrance modules being inserted into air freshener channels.
Figure 1B:
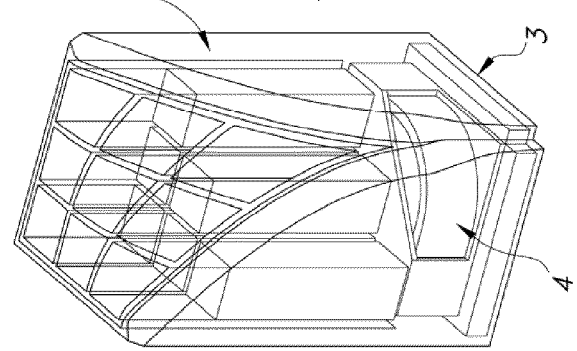
FIG. 1b is a cutaway view of an air freshener according to one embodiment of the disclosure.
Figure 1C:
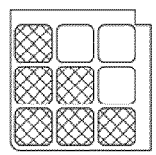
FIG. 1c is an illustrative view of one embodiment of the present disclosure showing an air freshener without fragrance modules.
Figure 1D:
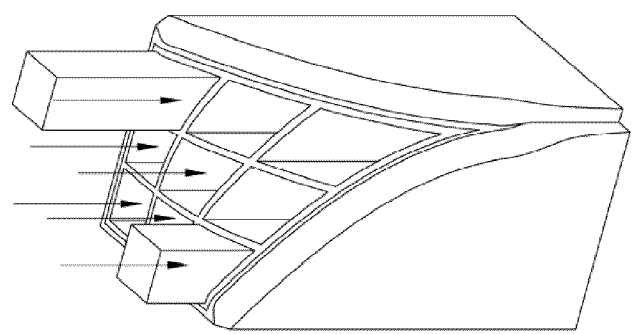
FIG. 1d is a top view of one embodiment of the present disclosure showing a number of fragrance module receptacles and a number of receptacles available for other uses.
Figures 2A, 2B, 2C, 2D:
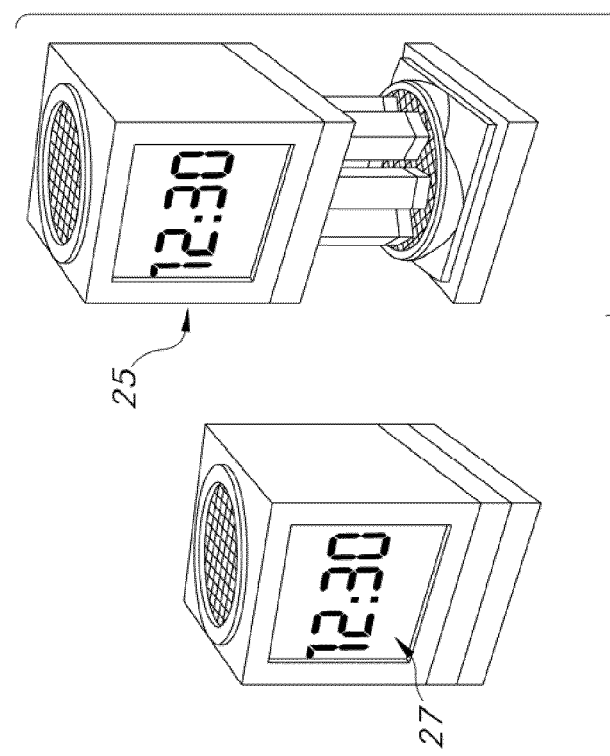
FIG. 2a is an illustrative view of another embodiment of the air freshener of the present disclosure.
FIG. 2b is an exploded view of the embodiment of the air freshener of the present disclosure.
FIG. 2c is an exploded view of the embodiment of the air freshener of the present disclosure showing a plurality of fragrance modules contained with the air freshener.
FIG. 2d is an exploded view of the embodiment of the air freshener of the present disclosure showing a plurality of fragrance module receptacles contained within the air freshener.
Figure 3D:
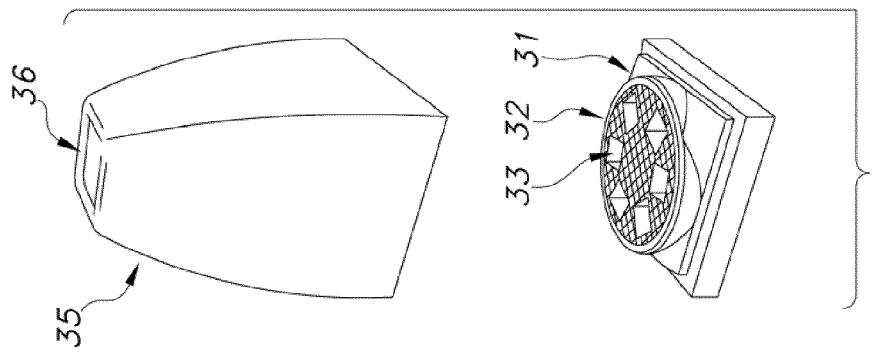
FIG. 3d is yet another exploded view of the embodiment showing a number of receptacles contained with the base portion of the air freshener for locating a number of fragrance modules.
Figure 3C:
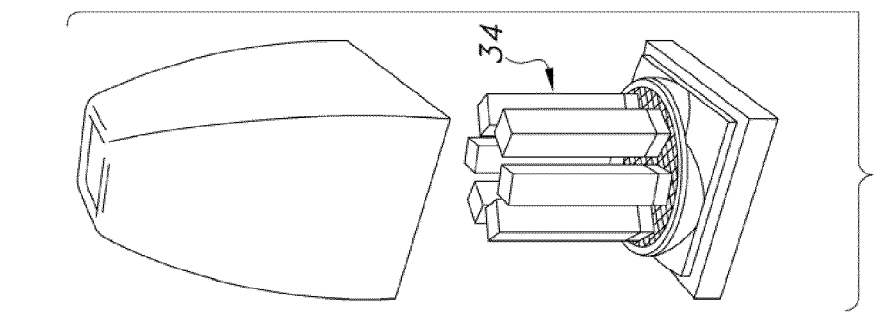
FIG. 3c is another exploded view of the embodiment showing a number of fragrance modules housed within the air freshener.
Figure 3B:
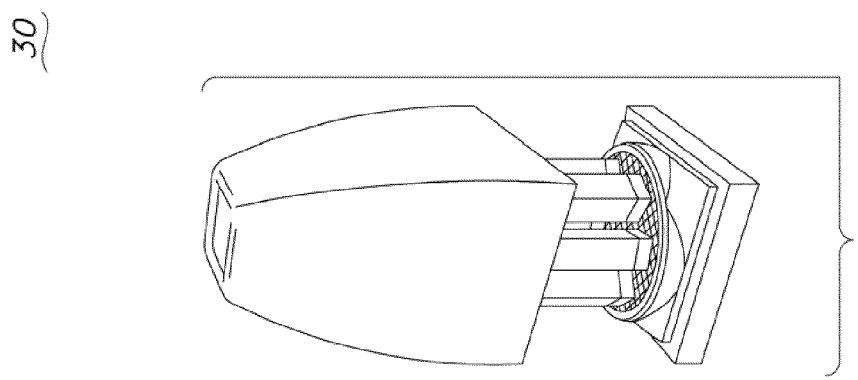
FIG. 3b is an exploded view of an embodiment of the air freshener of the present disclosure, showing a number of fragrance modules contained within the air freshener.
Figure 3A:
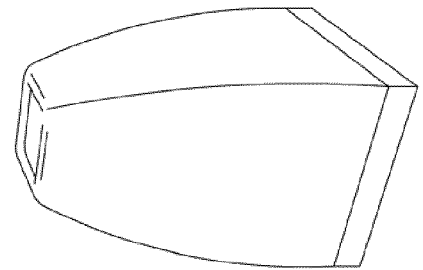
FIG. 3a is an illustrative view of another embodiment of the air freshener of the present disclosure.
Figure 4D:
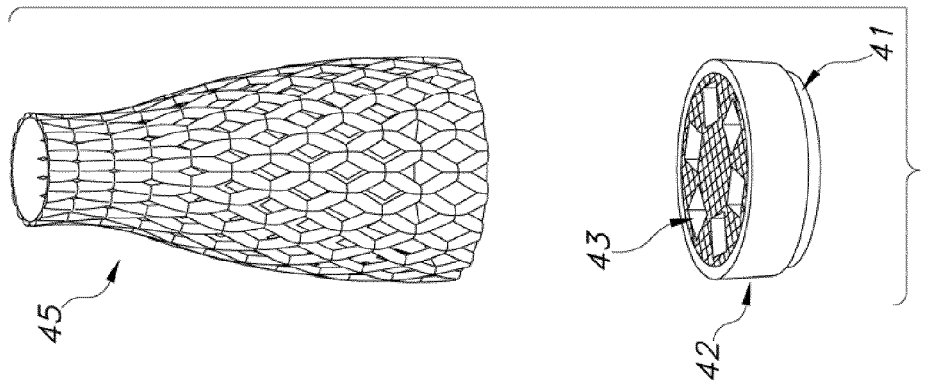
FIG. 4d is an exploded view of the embodiment without the fragrance modules showing the receptacles within the base portion of the air freshener where the modules are installed.
Figure 4C:
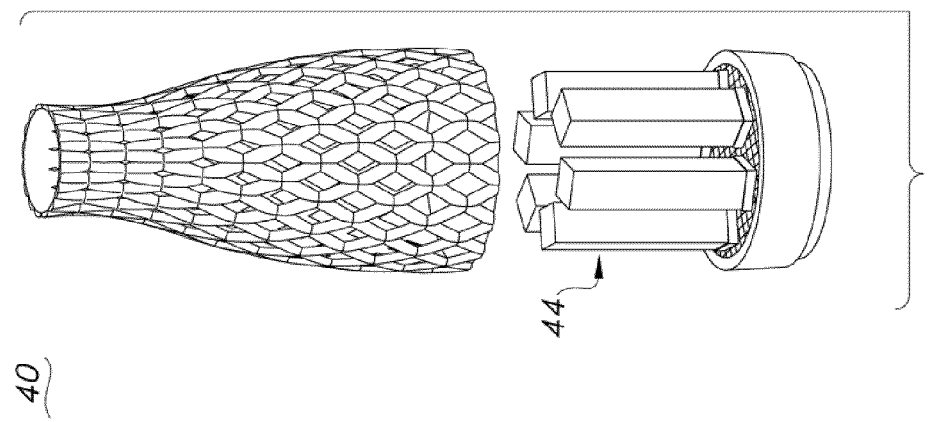
FIG. 4c is an exploded view of the embodiment showing the upper portion of the air freshener as positioned to enclose the fragrance modules.
Figure 4B:
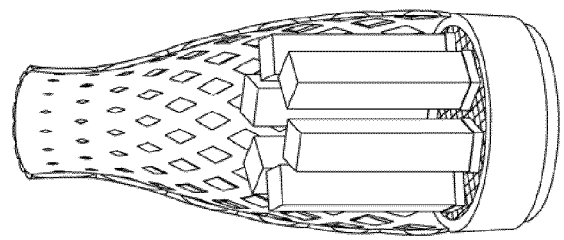
FIG. 4b is a cutaway view of the embodiment showing a number of fragrance modules housed within the air freshener.
Figure 4A:
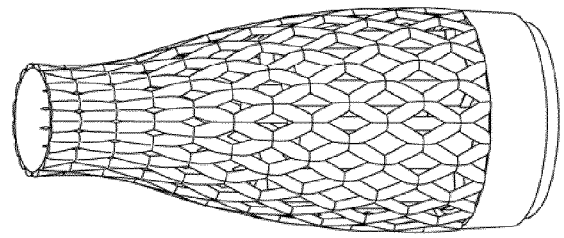
FIG. 4a is an illustrative view of one embodiment of the air freshener of the present disclosure.

Referring now to FIGS. 1a-1d, air freshener 10 according to one embodiment of the disclosure is shown. Housing 1 includes 4 sides, a base, and in this embodiment, an open top with a plurality of channels or receptacles 2 for inserting fragrance modules 5. Housing 1 may be of many designs to compliment decor, or be styled after other objects, such as figurines, statues, plants, animals, or other decorative objects. Further, housing 1 may incorporate power elements such as solar arrays or inductive coils for providing power to the air freshener. Channels 2 allow a user to insert fragrance modules into air freshener 10. These channels may use gravity to retain the modules in position, or may include other retention devices, such as magnets, tabs, adhesive, or other physical retaining means to prevent the modules from exiting the channels unless desired by the user.

Control unit 3, located at the base of housing 1 in this embodiment, contains the power supply for the air freshener 10, such as a battery, inductive or other electrical power (AC mains or DC). Also included in control unit 3 is other sensors and programmable memory which allow for user-defined operation of the air freshener. For example, the control unit 3 may contain a clock/timer, so that the user may program the operation of the air freshener to specific time periods. This conserves energy and the fragrance module(s) and allows the user to only experience the fragrance at specifically chosen times. For example, the user may desire to experience the fragrance from 6 pm to 9 pm daily. Further, if multiple fragrance modules are used, the user can select some or all of the fragrance to be dispensed at the same or different times according to the user's preferences. Additionally, control unit 3 may contain other logic to interpret sensor information. For example, a motion or thermal sensor located within the air freshener may detect a user in the local environment. After receiving such a signal, the control unit determines which fragrance to dispense, and for what time duration—such as one hour, 6 hours, as long as a user is present, and other appropriate parameters. A photocell may also be connected to control unit 3, so that the fragrances are only dispensed by the air freshener during daytime hours, or nighttime hours, if desired. Also, a combination of the sensors and timer may be used to create a variety of operational parameters. For example, a certain fragrance combination may only be active on weekends when users are detected during daylight hours.

Fragrance dispersal unit 4 is located within housing 1 of air freshener 10. Dispersal unit 4 may be a fan and/or heating element, which accelerates the vaporization of the fragrance contained in the fragrance modules 5. If the dispersal unit is a fan, air is drawn into the housing 1 through various air intakes (not shown) then accelerated around and among the fragrance modules, increasing the rate of vaporization, and spreading the fragrance in the environment once the fragrance breaches the housing boundaries. If the dispersal unit 4 is a heating element, the control unit activates the heating element, causing the fragrance modules to become warm, increasing the vaporization of the fragrant materials contained within housing 1. As the heat generated by the element surpasses the ambient room temperature, the heated fragrance vapor exits housing 1 and enters the environment. Further, a combination fan and heater dispersal unit may be used, for a variety of reasons, including increased dispersal rate of fragrance, housing design and layout, or application utilizing the air freshener, such as an outdoor environment, or low temperature environment.

Fragrance modules 5 may be of a variety of shapes and sizes, dependent upon the housing and channel configurations. In the embodiment shown in FIGS. 1*a*-1*d*, the modules 5 are long rectangular shapes, but the modules may be in a variety of forms, such as cards, cubes, cylinders, spheres, or any other geometric shape. The modules are impregnated with fragrance and may be color coded to correspond to perceived color of the fragrance. For example, a pine scented module may be colored green for ease of identification. However, in other applications where the modules have an additional design element feature; that is, they are visible in normal operation, the modules may be colored or designed differently to correspond to the particular housing or channel configuration. The modules 5 or channels 2, or both, may include a retention mechanism that prevents the modules from exiting the housing unintentionally, such as if the air freshener 10 is toppled. However, the modules are fully able to be removed at the user's discretion, such as fragrance exhaustion or a new fragrance is desired.

Referring now to FIGS. 2*a*-2*d*, another embodiment of the present disclosure is shown, air freshener 20. Control unit 21 also acts as the base in this embodiment, and includes a plurality of sensors, a power supply, and programmable logic unit as disclosed above. Adjacent to control unit 21 is fan/heater element 22. In this embodiment, the fan/heater element incorporates a plurality of sockets 23 for retaining a plurality of fragrance modules 24. If element 22 includes a fan, air is drawn from vents (not shown) surrounding the control unit/base 21, and is propelled upward past modules 24, increasing the fragrance vaporization rate and propelling the fragrance into the environment through vent 26, discussed below. If element 22 includes a heater, the control unit, operating either the fan or heater element, or both, activates the heating element, which causes the temperature of the modules 24 to increase above ambient room temperature. This heating causes the fragrance within the modules to vaporize into the air, and escape through the vent 26. As previously discussed, the plurality of fragrance modules 24 may be of one scent, or can be of a number of scents of the user's selection. In this embodiment, the modules are held securely in the control unit/base by the sockets or receptacles 23, using a number of mechanical methods, such as a snap fit, adhesive, or a mating threaded arrangement.

In this embodiment, air freshener 20 includes a housing 20 incorporating a vent 26 and a display 27. The vent 26 is located at the top of this housing 20 in this embodiment, but may be located in other positions, dependent upon the design of the housing. For example, a vent or vents may be located about a spherical shape, or at the corners of a cube shape. Display 27 as disclosed in this embodiment, provides information for a clock, radio, MP3 player, or other operational information relating to the air freshener 20. The display is connected electronically to the control unit 21, such that a user may use input devices, such as buttons (not shown) to program the operation of the air freshener, set the clock, alarm, or other appropriate features. Operational information shown on the display may include fragrance life, battery life, alarm status, am/pm, or other relevant information. The display may also show a program menu (not shown) allowing the user to preset operational commands into the air freshener. For example, if a clock is included in the air freshener display 27, additional clock features, such as atomic clock setting, world time, or a calendar may also be included. Additionally, display 27 may also provide weather information, such as indoor/outdoor temperature using a temperature sensor integrated into control unit 21.

Referring now to FIGS. 3*a*-3*d*, another embodiment of the present disclosure is shown, air freshener 30. Control unit 31 also acts as a base in this embodiment, and includes a plurality of sensors, a power supply, and programmable logic unit as disclosed above. Adjacent to control unit 31 is fan/heater element 32. In this embodiment, the fan/heater element incorporates a plurality of sockets 33 for retaining a plurality of fragrance modules 34. If element 32 includes a fan, air is drawn from intakes (not shown) surrounding the control unit/base 31, and is propelled upward past modules 34, increasing the fragrance vaporization rate and propelling the fragrance into the environment through vent 36, discussed below. If element 32 includes a heater, the control unit, operating either the fan or heater element, or both, activates the heating element, which causes the temperature of the modules 34 to increase above ambient room temperature. This heating causes the fragrance within the modules to vaporize into the air, and escape through the vent 36, integrated into housing 35. As previously disclosed above, the plurality of fragrance modules 34 may be of one scent, or of a number of scents of the user's selection. In this embodiment, the modules are held securely in the control unit/base by the sockets or receptacles 33, using a number of mechanical methods, such as a snap fit, adhesive, or other secure arrangement.

Referring now to FIGS. 4a-4d, another embodiment of the present disclosure is shown, air freshener 40. Control unit 41 also acts as a base in this embodiment, and includes a plurality of sensors, a power supply, and programmable logic unit as disclosed above. Adjacent to control unit 41 is fan/heater element 42. In this embodiment, the fan/heater element incorporates a plurality of sockets 43 for retaining a plurality of fragrance modules 44. If element 42 includes a fan, air is drawn from vents (not shown) surrounding the control unit/base 41, and is propelled upward past modules 44, increasing the fragrance vaporization rate and propelling the fragrance into the environment through vent 46, discussed below. If element 42 includes a heater, the control unit, operating either the fan or heater element, or both, activates the heating element, which causes the temperature of the modules 44 to increase above ambient room temperature. This heating causes the fragrance within the modules to vaporize into the air, and escape through housing 45. As previously disclosed above, the plurality of fragrance modules 44 may be of one scent, or can be of a number of scents of the user's selection. In this embodiment, the modules are held securely in the control unit/base by the sockets 43, using a number of mechanical methods, such as a snap fit, adhesive, or a mating threaded arrangement.

Referring now to FIGS. 5a-5c, another embodiment of the present disclosure is shown, air freshener 50. Control unit 51 also acts as a base in this embodiment, and includes a plurality of sensors, a power supply, and programmable logic unit as disclosed above. Adjacent to control unit 51 is fan 52, which intakes air from surrounding vents (not shown) and propels air upwards through the fragrance module 54. Fan door 53 allows for access to the fan 52 to service and maintenance. Fragrance module 54 may also incorporate, in this embodiment, a filter element portion for filtering air propelled through it by fan 52. These modules may be of different sizes, so as to be contained within housing 56. Further, the modules 54 may be segmented to include more than one fragrance within each module, rather than a single module for each fragrance. In this way, modules may be switched according to the strength or blend of the fragrance desired by the user.

Referring now to FIGS. 6a-6b, another embodiment of the present disclosure is shown, air freshener 60. Control unit 61 is incorporated into one portion of air freshener 60 and includes a plurality of sensors, a power supply, and programmable logic unit as disclosed above. A fan or heating element (not shown) is located adjacent to the control unit, for propelling air through the air freshener and fragrance modules 64 or for heating the modules to cause the fragrance to be released into the environment. The modules in this embodiment are card-like and are intended to be inserted into the air freshener through slots 63 located about housing 62. The modules also may include an optional filtering component, which purifies the air through removing particulates while also releasing fragrance to the environment.

Referring now to FIGS. 7a-7c, another embodiment of the present disclosure is shown, air freshener 70. Control unit 71 is incorporated into a portion of the air freshener that rests within housing frame 72. The control unit includes a plurality of sensors, a power supply, and programmable logic unit as disclosed above. Fan/heating element 73 is located adjacent to the control unit for propelling air through the air freshener and fragrance modules 74 or for heating the modules to cause the fragrance to be released into the environment. The modules in this embodiment are nestable, to be held within housing 74. The modules also may include filtering or other air flowable passages to permit air to pass upward through each module, gaining fragrance with each ascending module, until the top module is reached and the fragrance escapes to the environment.

Figure 8B:
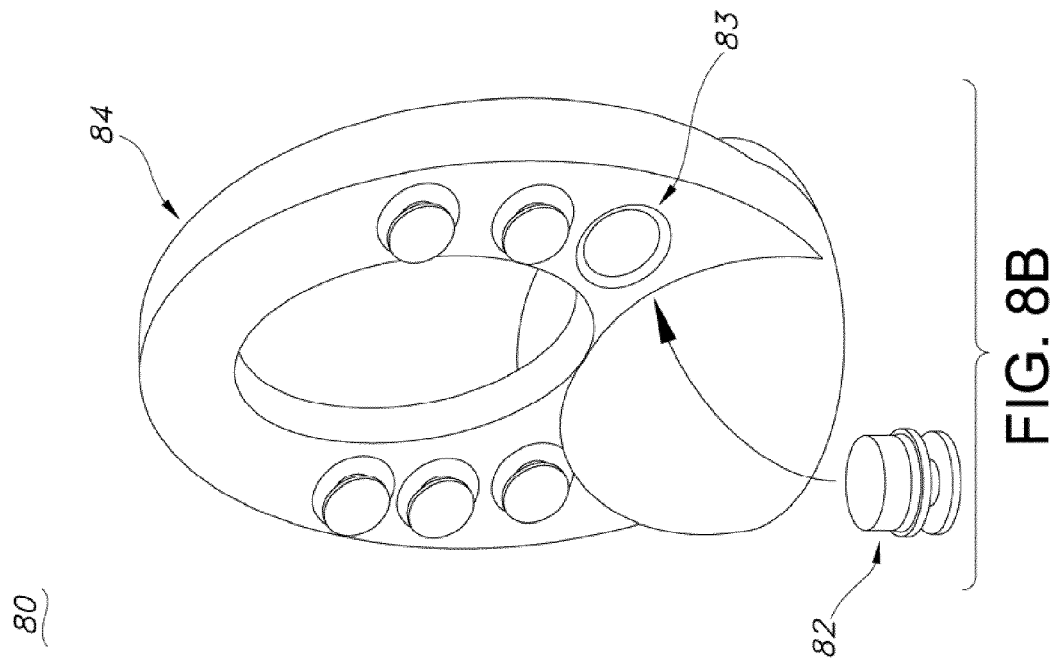
FIG. 8b is another illustrative view of the embodiment including a number of fragrance modules for installation within the air freshener of the present disclosure.
Figure 8A:
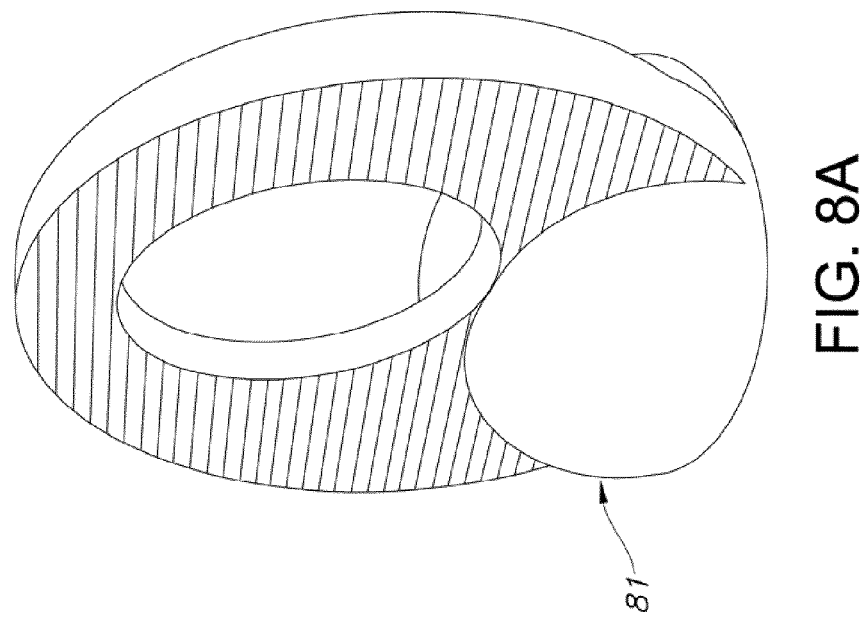
FIG. 8a is an illustrative view of one embodiment of the air freshener of the present disclosure.

FIGS. 8a-8b illustrate another embodiment of the present disclosure, air freshener 80. Control unit and integrated base 81 include fan/heater element (not shown). The control unit includes a plurality of sensors, a power supply, and programmable logic unit as disclosed above. The fan/heating element propels air through the base and fragrance modules 82 or for heating the modules to cause the fragrance to be vaporized into the air, which is drawn into housing 84 through a plurality of vents, where it is then internally routed to pass around modules 82, which are emitting fragrance. Sockets 83 securely yet selectively hold the modules in place after installation by a user. The now fragrance-enhanced air then exits the housing 84 into the environment.

Figure 9A:
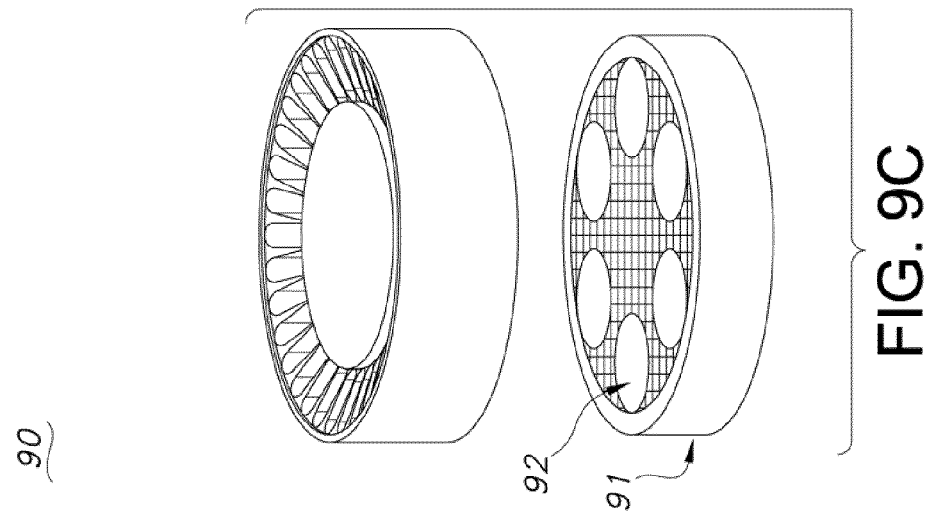
FIG. 9a is an illustrative view of one embodiment of the air freshener of the present disclosure.
Figure 9B:
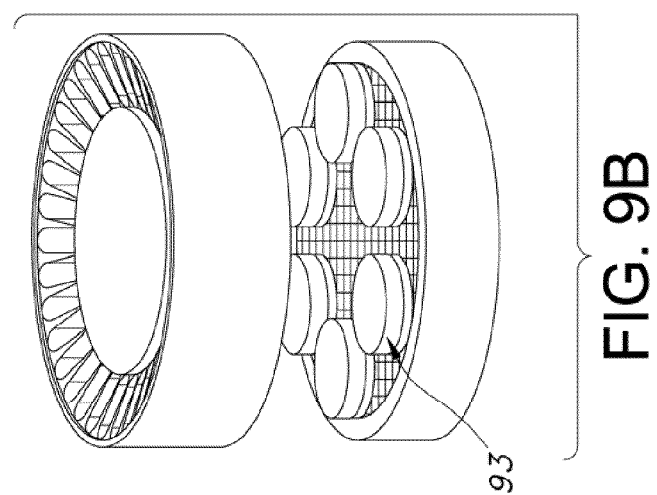
FIG. 9b is an exploded view of the embodiment showing a number of fragrance modules contained within the air freshener of the present disclosure.
Figure 9C:
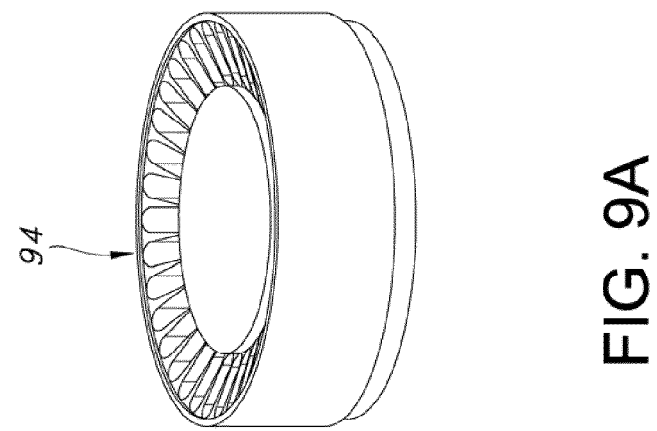
FIG. 9c is another exploded view of the embodiment showing a number of receptacles for the fragrance modules with in the air freshener of the present disclosure.

FIGS. 9a-9c illustrate another embodiment of the present disclosure, air freshener 90. Control unit and integrated base 91 include fan/heater element (not shown). The control unit includes a plurality of sensors, a power supply, and programmable logic unit as disclosed above. The fan/heating element propels air and/or heat through the base and fragrance modules 93, which are held in place securely but selectively by sockets 92. Housing 94 is attached to base 91 in normal operation, but can be easily removed for accessing the fragrance modules. Further, housing 94 also includes a vent for allowing freshened air to exit into the environment. The vent also adjusts the air flow rate according to the user's preferences.

FIGS. 10a-10f illustrate another embodiment of the present disclosure, air freshener 100. Control unit and integrated base 101 include fan/heater element 102. The control unit includes a plurality of sensors, a power supply, and programmable logic unit as disclosed above. The fan/heating element propels air and/or heat through the base and fragrance modules 103, which, in this embodiment, are disk-shaped, and held in place by module holder 105, which is mounted to control unit and base 101, and includes air flow passages to allow forced and/or heated air to pass through it to contact the modules 103, which can be arranged in a stacked array 104 according to the user's preferences. For example, a number of modules can be of the same fragrance or of different fragrances. Housing 106 includes a vent (not shown) for permitting air flow outside of the air freshener. The vent may be incorporated into the housing design, such as with a plurality of slots in geometric fashion, and a regulator function may be included to meter the air flow through the housing and thus into the environment.

FIGS. 11a-11c illustrate another embodiment of the present disclosure, air freshener 110. Control unit 111 includes a fan/heater element. The control unit includes a plurality of sensors, a power supply, and programmable logic unit as disclosed above. Fragrance modules 112 are inserted into trays 113 which are stackable upon each other, and are topped with vent lid 114, which has an adjustable air flow vent and an access handle. Housing 115, within which is located control unit 111, encloses modules 112 and trays 113 such that only vent lid 114 is exposed when the air freshener is assembled for normal operation. By alternating the type of modules 112, the user can experience different levels and intensities of fragrance, and vent lid 114 can further adjust the air flow to the environment.

Figure 12C:
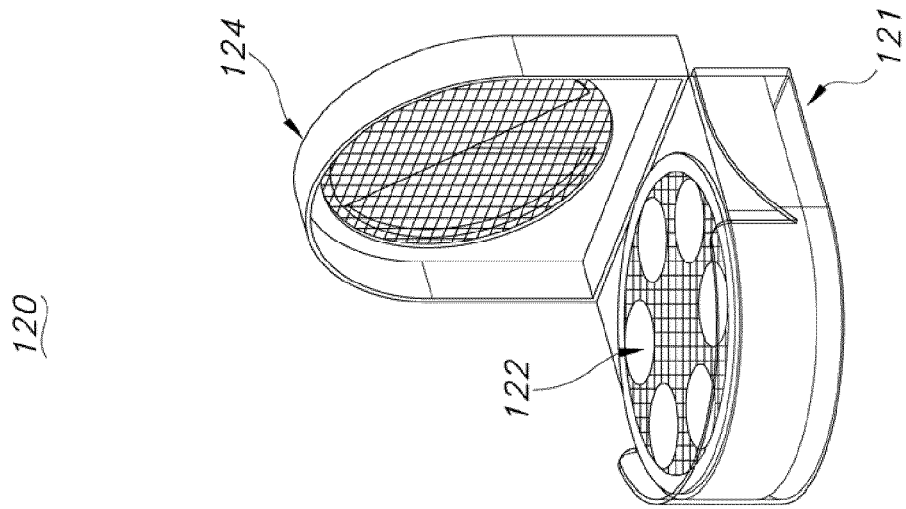
FIG. 12c is yet another illustrative view of the embodiment showing a number of receptacles within the air freshener for receiving the fragrance modules.
Figure 12B:
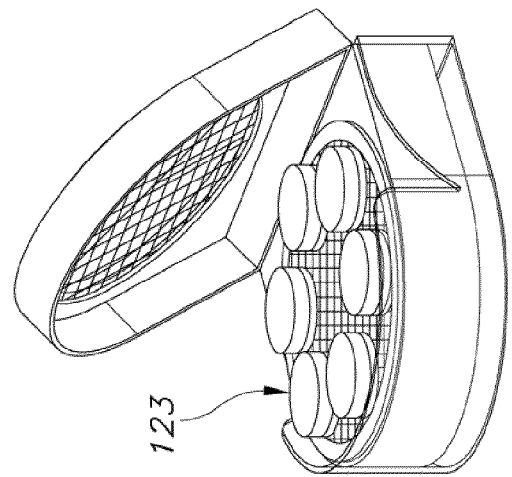
FIG. 12b is another illustrative view of the embodiment showing a number of fragrance modules located with the air freshener.
Figure 12A:
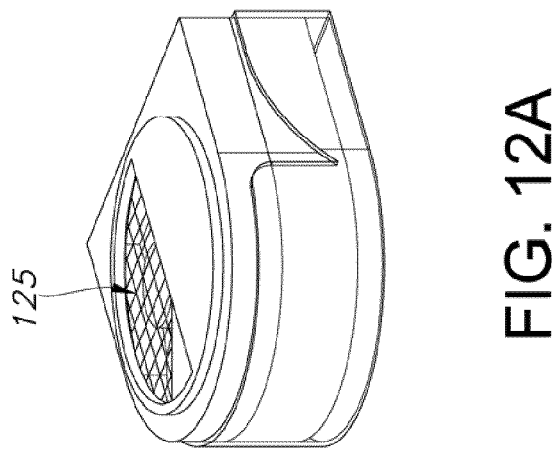
FIG. 12a is an illustrative view of one embodiment of the air freshener of the present disclosure.

FIGS. 12*a*-12*c* illustrate another embodiment of the present disclosure, air freshener 120. Control unit and integrated base 121 include fan/heater element (not shown). The control unit includes a plurality of sensors, a power supply, and programmable logic unit as disclosed above. The fan/heating element propels air and/or heat through the base and fragrance modules 123, which are held in place securely but selectively by sockets 122. Lid 124 is hingedly attached to base 121 in normal operation, but can be easily removed for accessing the fragrance modules. Further, the lid also includes vent 125 for allowing freshened air to exit into the environment. The vent also adjusts the air flow rate according to the user's preferences.

Figure 13:
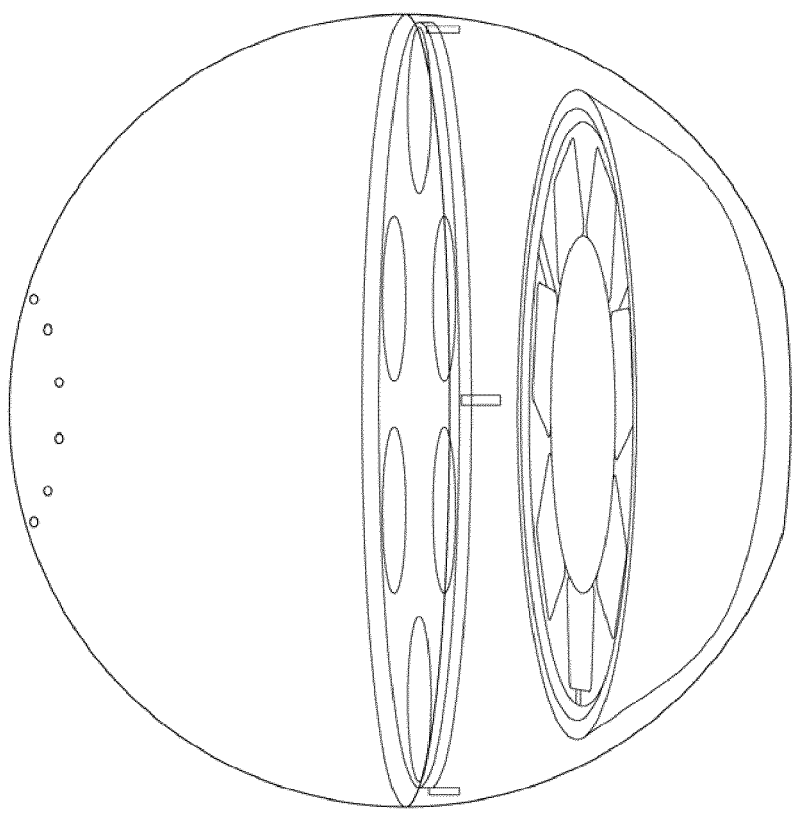
FIG. 13 is a cutaway view of one embodiment of the air freshener of the present disclosure.

FIG. 13 illustrates another embodiment of the present disclosure, this particular embodiment of the air freshener 130 is the general form of a sphere. Fan element 131, which may also include a heater or a heater without a fan, is located in the lower portion of the sphere housing 132. Air intakes adjacent to the fan/heater element allow air from outside the air freshener to enter, where the air is heated and/or propelled around a plurality of fragrance modules, or disks 133, contained in fragrance disk holder 134, which is securely attached to the housing 132, and contains a plurality of passages through which air may pass. The now-freshened air rises through the sphere housing 132 until it reaches the upper portion of the housing, which contains a plurality of fragrance vents 135, whereby the freshened air escapes the housing into the environment. Additional sensors may be placed about the housing as desired, to measure such attributes as light level (photocell), temperature (thermometer), or motion (optical or infrared).

FIGS. 14*a*-14*b* illustrate yet another embodiment of the present disclosure, air freshener 140. Fan with optional heater element 141, or heater element alone, is located in the interior of the air freshener 140, adjacent to a plurality of fragrance modules, or disks 142. Airflow path 143 connects fan 141 and modules 142 and channels air which has been propelled and/or heated, from the environment, through the path 143, into contact with the modules 142, and finally returning to the environment freshened air. Housing 144 contains the fan 141, modules 142, and flow path 143, and is supported in this embodiment by decorative leg stands 145, but other arrangements may be used, dependent upon the exterior styling of the housing and accompanying supports.

If not otherwise stated herein, it is to be assumed that all patents, patent applications, patent publications, and other publications (including web-based publications) mentioned and cited herein are hereby fully incorporated by reference herein as if set forth in their entirety herein.

Although illustrative embodiments of the present disclosure have been described herein with reference to the accompanying drawings, it is to be understood that the disclosure is not limited to those precise embodiments, and that various other changes and modifications may be affected therein by one skilled in the art without departing from the scope or spirit of the disclosure.

The invention claimed is:

1. An air freshener with customization for fragrance strength and character, said air freshener comprising:
    a fragrance dispersal unit;
    a control unit, for controlling the operation of said dispersal unit;
    a power source, for providing electrical power to said dispersal unit and said control unit;
    a plurality of fragrance modules, each of said fragrance modules containing a fragrance and being configured to disperse said fragrance by vaporization, each of said fragrance modules having a longitudinal axis;
    a plurality of fragrance module sockets, for securing said fragrance modules in an air flow path adjacent said fragrance dispersal unit, said sockets securing said fragrance modules in parallel with one another and with said longitudinal axes extending parallel to a general direction of said flow path;
    a vent for regulating air flow; and
    a housing, for providing a location for said dispersal unit, said control unit, said modules, said sockets, and said vent.

2. The air freshener of claim 1, wherein said fragrance dispersal unit is a fan.

3. The air freshener of claim 1, wherein said fragrance dispersal unit is a heater element.

4. The air freshener of claim 1, wherein said fragrance dispersal unit is a heater element and a fan.

5. The air freshener of claim 1, wherein said power source is a battery.

6. The air freshener of claim 1, wherein said power source is a connection to AC power.

7. The air freshener of claim 1, wherein said power source is a connection to DC power.

8. The air freshener of claim 1, wherein said power source is a solar array.

9. The air freshener of claim 1, wherein said power source is an inductive coil.

10. The air freshener of claim 1, wherein said power source includes an inductive coil power base and a secondary coil included within said housing.

11. The air freshener of claim 1, wherein said control unit contains a microcomputer and a plurality of sensors for operation and customization of said air freshener.

12. The air freshener of claim 1, wherein said control unit contains a clock/timer device.

13. The air freshener of claim 1, wherein said control unit includes a music playing device.

14. The air freshener of claim 1, wherein said control unit includes a lighting control device.

15. The air freshener of claim 1, wherein said fragrance modules include a filter element.

16. A method of freshening air with a plurality of fragrances, said method comprising:
    in-taking air from the environment into an air freshener;
    accelerating said air using a fan;
    heating said air with a heater element;
    exposing said air to a plurality of fragrance modules within an air flow path, said fragrance modules containing a fragrance and being configured to disperse said fragrance by vaporization, each of said fragrance modules having a longitudinal axis, said fragrance modules arranged in parallel with one another and with said longitudinal axes extending parallel to said air flow path, whereby heated air extends along a longitudinal extent of each of said fragrance modules; and
    propelling said air to the environment.

17. The method of claim 16, further comprising utilizing a regulator vent to control the amount of air entering the environment.

18. The method of claim 16, further comprising programming of a control unit within said air freshener to customize the operation of said air freshener.

19. A method of freshening air with a plurality of fragrances, said method comprising:

in-taking air from the environment into an air freshener;

accelerating said air using a fan;

heating a plurality of fragrance modules to promote volatilization;

positioning said modules in the air flow provided by said fan, said modules containing a fragrance and being configured to disperse said fragrance by vaporization, each of said modules having a longitudinal axis, said modules arranged in parallel with one another and with said longitudinal axes extending parallel to said air flow, whereby heated air extends along a longitudinal extent of each of said modules; and providing an exit for said air flow to the environment.

20. The method of claim 19 further comprising programming of a control unit within said air freshener to customize the operation of said air freshener.

* * * * *